(12) United States Patent
Willis

(10) Patent No.: US 7,374,537 B2
(45) Date of Patent: *May 20, 2008

(54) PERFORMING ULTRASOUND RANGING IN THE PRESENCE OF ULTRASOUND INTERFERENCE

(75) Inventor: N. Parker Willis, Atherton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 262 days.

This patent is subject to a terminal disclaimer.

(21) Appl. No.: 10/951,853

(22) Filed: Sep. 27, 2004

(65) Prior Publication Data

US 2005/0038341 A1 Feb. 17, 2005

Related U.S. Application Data

(63) Continuation of application No. 10/214,441, filed on Aug. 6, 2002, now Pat. No. 6,805,132.

(51) Int. Cl.
*A61B 8/00* (2006.01)
*G01S 15/00* (2006.01)

(52) U.S. Cl. .......................... 600/438; 367/99
(58) Field of Classification Search ........ 600/437–438, 600/443–447, 454–456, 459–471
See application file for complete search history.

(56) References Cited

U.S. PATENT DOCUMENTS

| | | | |
|---|---|---|---|
| 3,795,911 A | 3/1974 | Hammack | |
| 3,893,064 A | 7/1975 | Nishihara | |
| 3,985,030 A * | 10/1976 | Charlton | 73/290 V |
| 4,528,651 A * | 7/1985 | Brock et al. | 367/99 |
| 4,574,368 A | 3/1986 | Lipschutz | |
| 4,596,144 A * | 6/1986 | Panton et al. | 73/620 |
| 4,679,175 A * | 7/1987 | Eder et al. | 367/98 |
| 4,821,569 A | 4/1989 | Soltz | |
| 4,993,427 A | 2/1991 | Barr et al. | |
| 5,036,477 A | 7/1991 | Foster et al. | |
| 5,142,506 A | 8/1992 | Edwards | |
| 5,260,910 A * | 11/1993 | Panton | 367/99 |
| 5,319,611 A * | 6/1994 | Korba | 367/98 |
| 5,321,668 A | 6/1994 | Rouquette | |
| 5,373,482 A | 12/1994 | Gauthier | |
| 5,418,758 A * | 5/1995 | Webster | 367/101 |

(Continued)

*Primary Examiner*—Francis J. Jaworski
(74) *Attorney, Agent, or Firm*—Vista IP Law Group LLP

(57) ABSTRACT

A distance measuring system comprises first and second transducers, and an ultrasound ranging subsystem coupled to the first and second transducers for performing a plurality of distance measurements between the first and second transducers. The distance measurement system can have various applications, including medical applications, in which case, the first and second transducers can be mounted on a catheter. The distance measuring system further comprises a filter coupled to the ultrasound ranging subsystem for filtering ultrasound interference from the plurality of distance measurements (such as, e.g., eight), and outputting a distance based on the filtered distance measurements. The filter filters the ultrasound interference by selecting one of the plurality distance measurements, in which case, the outputted distance is the selected distance measurement. Because the ultrasound interference will typically represent itself as the shortest distance measurement, the selected distance measurement is preferably greater than the minimum distance measurement (such as, e.g., the maximum distance measurement), thereby filtering the ultrasound interference out.

50 Claims, 13 Drawing Sheets

U.S. PATENT DOCUMENTS

| | | |
|---|---|---|
| 5,453,932 A | 9/1995 | Brabec |
| 5,473,934 A | 12/1995 | Cobb |
| 5,515,853 A | 5/1996 | Smith et al. |
| 5,671,190 A | 9/1997 | Kroemer et al. |
| 5,779,638 A | 7/1998 | Vesely et al. |
| 5,793,704 A | 8/1998 | Freger |
| 5,841,392 A * | 11/1998 | Kishimoto .................. 342/125 |
| 6,053,868 A | 4/2000 | Geistert et al. |
| 6,202,034 B1 | 3/2001 | Li |
| 6,216,027 B1 | 4/2001 | Willis et al. |
| 6,230,042 B1 | 5/2001 | Slettenmark |
| 6,246,898 B1 * | 6/2001 | Vesely et al. ................ 600/424 |
| 6,298,261 B1 | 10/2001 | Rex |
| 6,545,946 B1 | 4/2003 | Huss et al. |
| 6,771,560 B2 * | 8/2004 | Lyon et al. .................... 367/13 |
| 6,805,132 B2 * | 10/2004 | Willis ......................... 128/899 |

\* cited by examiner

PERFORMING ULTRASOUND RANGING IN THE PRESENCE OF ULTRASOUND INTERFERENCE

RELATED APPLICATION DATA

This application is a continuation of U.S. patent application Ser. No. 10/214,441, filed Aug. 6, 2002, now U.S. Pat. No. 6,805,132.

FIELD OF THE INVENTION

The invention relates generally to ultrasound ranging, and more particularly to systems and methods for performing ultrasound ranging in the presence of ultrasound interference.

BACKGROUND OF THE INVENTION

Ultrasound ranging is a technique for computing the distance between two ultrasound transducers. The principle of ultrasound ranging is illustrated in FIG. 1, which shows two ultrasound transducers 10,20 separated by a distance. One of the ultrasound transducers is designated as a transmitting transducer 10 and the other is designated as a receiving transducer 20. To measure the distance between the transducers 10,20, the transmitting transducer 10 transmits an ultrasound pulse 25, which is detected by the receiving transducer 20. The distance, d, between the transducers 10,20 is computed as $$d = v\tau$$

where v is the velocity of the ultrasound pulse 25 in the medium between the transducers 10,20 and $\tau$ is the time of flight of the ultrasound pulse 25 in traveling from the transmitting transducer 10 to the receiving transducer 20.

One application of ultrasound ranging is in ultrasound positional tracking to track the position of a device within a three-dimensional (3-D) coordinate system. Referring to FIG. 2, this is accomplished by mounting one or more ranging transducers 110 on the device 115 being tracked and providing four or more reference transducers 120-1 to 1204 that are spaced apart. In this particular example, the device 115 being tracked is a catheter tip. The ranging transducer 110 acts as a receiving transducer and each of the reference transducers 120-1 to 120-4 can act both as a receiving and transmitting transducer.

To establish the 3-D coordinate system, the reference transducers 120-1 to 120-4 are sequentially excited to transmit ultrasound pulses (not shown). When each reference transducer 120-1 to 120-4 transmits an ultrasound pulse, the other reference transducers 120-1 to 120-4 detect the ultrasound pulse. The relative distances between the reference transducers 120-1 to 120-4 are then computed by performing ultrasound ranging on each of the detected ultrasound pulses. The computed distances are then triangulated to determine the relative positions between the reference transducers 120-1 to 120-4 in 3-D space. The relative positions between the reference transducers 120-1 to 120-4 are then mapped onto the 3-D coordinate system to provide a reference for tracking the position of the ranging transducer 110 in the 3-D coordinate system.

To track the position of the ranging transducer 110, and hence the device 115 carrying the ranging transducer 110, in the 3-D coordinate system, the reference transducers 120-1 to 120-4 are sequentially excited to transmit ultrasound pulses. When each of the reference transducers 120-1 to 120-4 transmits an ultrasound pulse, the ranging transducer 110 detects the ultrasound pulse. The distance d1-d4 between the ranging transducer 110 and each of the reference transducers 120-1 to 120-4 is computed by performing ultrasound ranging on each of the detected ultrasound pulses. The computed distances are then triangulated to determine the relative position of the ranging transducer 110 to the reference transducers 120-1 to 120-4 in 3-D space. The position of the ranging transducer 110 in the 3-D coordinate system is then determined based on the relative position of the ranging transducer 110 to the reference transducers 120-1 to 120-4 and the known positions of reference transducers 120-1 to 1204 in the 3-D coordinate system.

An example of a tracking system using ultrasound ranging is the Realtime Position Management™ (RPM) tracking system developed commercially by Cardiac Pathways Corporation, now part of Boston Scientific Corp. The RPM system uses ultrasound ranging to track the positions of medical devices, including reference catheters, mapping catheters and ablation catheters.

Because ultrasound ranging relies on the transmission and detection of ultrasound pulses to measure distance, it is vulnerable to ultrasound interference from ultrasound sources, e.g., an ultrasound imager. For example, ultrasound interference may be detected by the receiving transducer 20 and misinterpreted as an ultrasound pulse from the transmitting transducer 10, producing an erroneous distance measurement.

Therefore, there is need for systems and methods that enable the use of ultrasound ranging in the presence of ultrasound interference.

SUMMARY OF THE INVENTION

The present inventions are directed to systems and methods that enable the use of ultrasound measuring equipment in the presence of ultrasound interference.

In accordance with a first aspect of the present inventions, a distance measuring system comprises first and second transducers, and an ultrasound ranging subsystem coupled to the first and second transducers for performing a plurality of distance measurements between the first and second transducers. By way of non-limiting example, the distance measuring system, in performing the distance measurements, comprises a pulse generator coupled to the first transducer for generating and transmitting transmit pulses to the first transducer, a threshold detector coupled to the second transducer for detecting receive pulses from the second detector, and measurement means (e.g., a digital counter) coupled to the pulse generator and the threshold detector. In this case, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

The distance measuring system further comprises a filter coupled to the ultrasound ranging subsystem for filtering ultrasound interference from the plurality of distance measurements (such as, e.g., eight), and outputting a distance based on the filtered distance measurements. The distance measurement system can have various applications, including medical applications, in which case, the first and second transducers can be mounted on a catheter.

In the preferred embodiment, the filter filters the ultrasound interference by selecting one of the plurality distance measurements, in which case, the outputted distance is the selected distance measurement. Because the ultrasound interference will typically represent itself as the shortest distance measurement, the selected distance measurement is preferably greater than the minimum distance measurement (such as, e.g., the maximum distance measurement), thereby filtering the ultrasound interference out.

Although the present inventions should not be so limited in its broadest aspects, the filter sequentially receives the distance measurements, and filters the ultrasound interference from the last N distance measurements. In this case, the filter may filter the last N distance measurements by selecting one of them. So that the system is more responsive to movements of the transducers, the filter can compute a distance variation of the N distance measurements, and compare the distance variation to a threshold value. The filter can then output the distance when the distance variation exceeds the threshold value, while outputting the most recent distance measurement received from the ultrasound ranging subsystem otherwise. In effect, the filtering is only accomplished when there is ultrasound interference, thereby providing more responsiveness to the distance measuring process. The distance variation computation can be accomplished in a variety of ways, including taking the difference between the maximum and minimum of the last N distance measurements, calculating the variance of the last N distance measurements, or calculating the second derivative of the last N distance measurements.

In accordance with a second aspect of the present inventions, a method for measuring the distance between two transducers comprises performing a plurality of distance measurements (e.g., eight) between the transducers. For example, the distance measurement can comprise exciting one of the transducers to transmit an ultrasound pulse, and measuring the time for the ultrasound pulse to reach the other transducer.

The method further comprises filtering ultrasound interference from the plurality of distance measurements, and outputting a distance based on the filtered distance measurements. The distance measurements can be filtered by, e.g., selecting one of the plurality distance measurements, in which case, the outputted distance will be the selected distance measurement. The selected distance measurement is preferably more than the minimum distance measurement, such as, e.g., the maximum distance measurement.

Although the present inventions should not be some limited in its broadest aspects, the distance measurements are sequentially received, and the ultrasound interference is filtered from the last N distance measurements. In this case, the last N distance measurements can be filtered by selecting one of them. So that the method is more responsive to movements of the transducers, a distance variation of the N distance measurements can be computed and compared to a threshold value. The distance can then be outputted when the distance variation exceeds the threshold value, while the most recent distance measurement received from the ultrasound ranging subsystem can be outputted otherwise, thereby providing for a more responsive method. The distance variation computation can be accomplished in a variety of ways, including taking the difference between the maximum and minimum of the last N distance measurements, calculating the variance of the last N distance measurements, or calculating the second derivative of the last N distance measurements.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
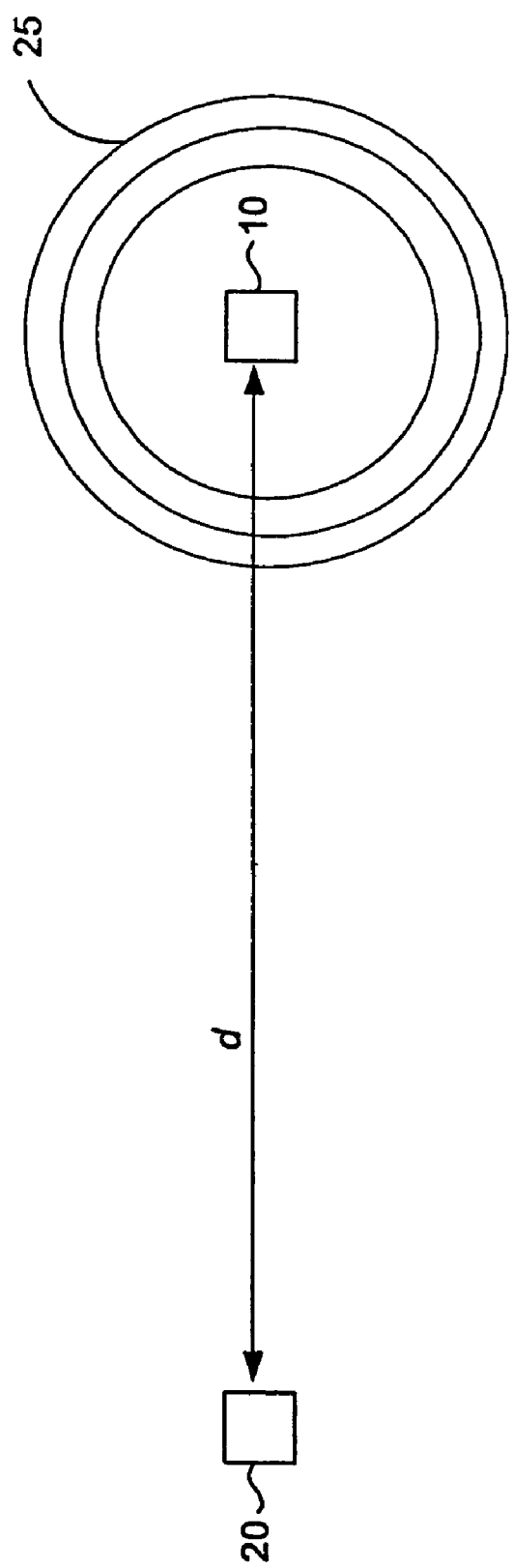
FIG. 1 is a diagram illustrating the principle of ultrasound ranging between two transducers.
Figure 2:
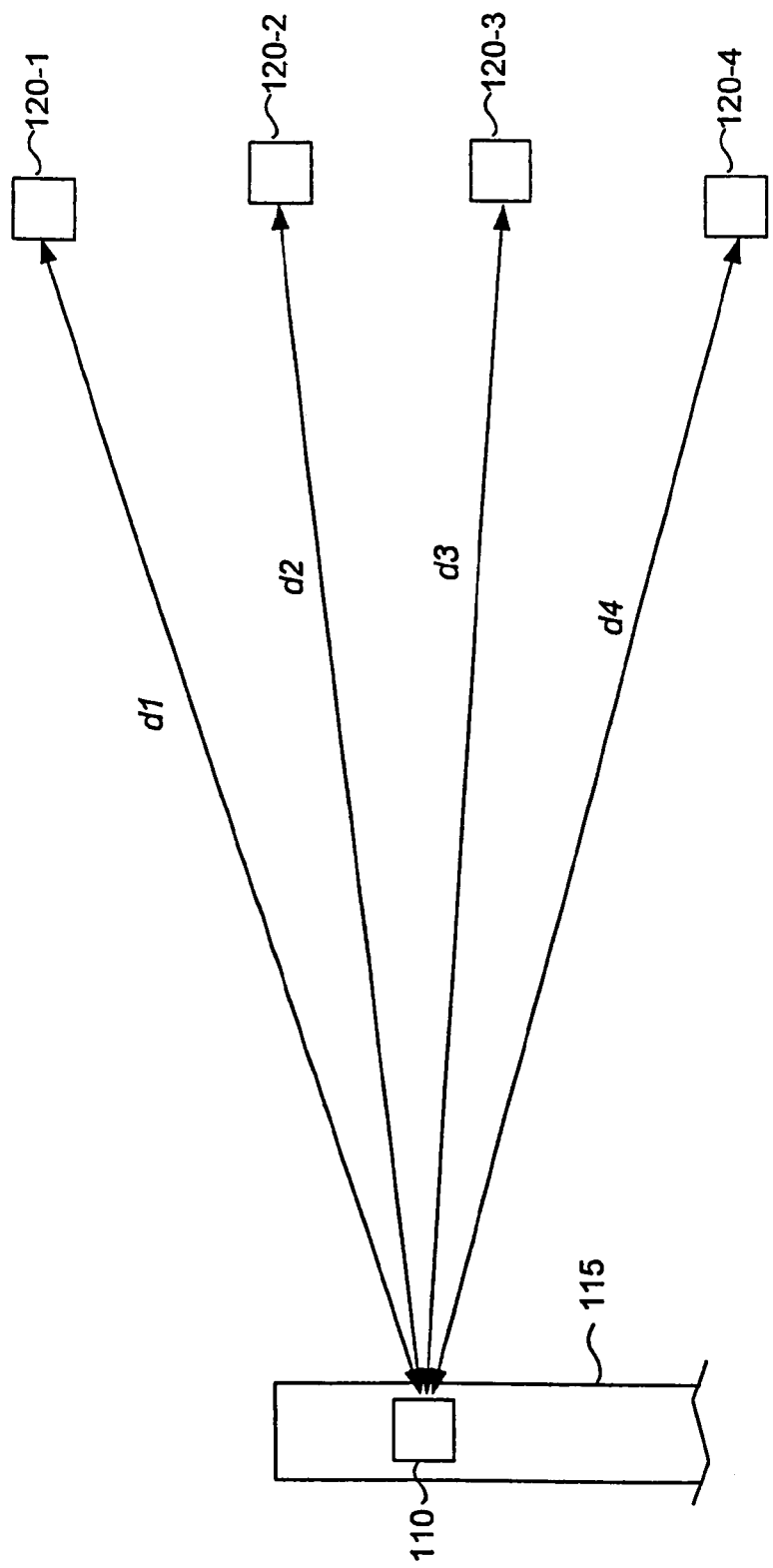
FIG. 2 is a diagram illustrating ultrasound positional tracking using ultrasound ranging.
Figure 3:
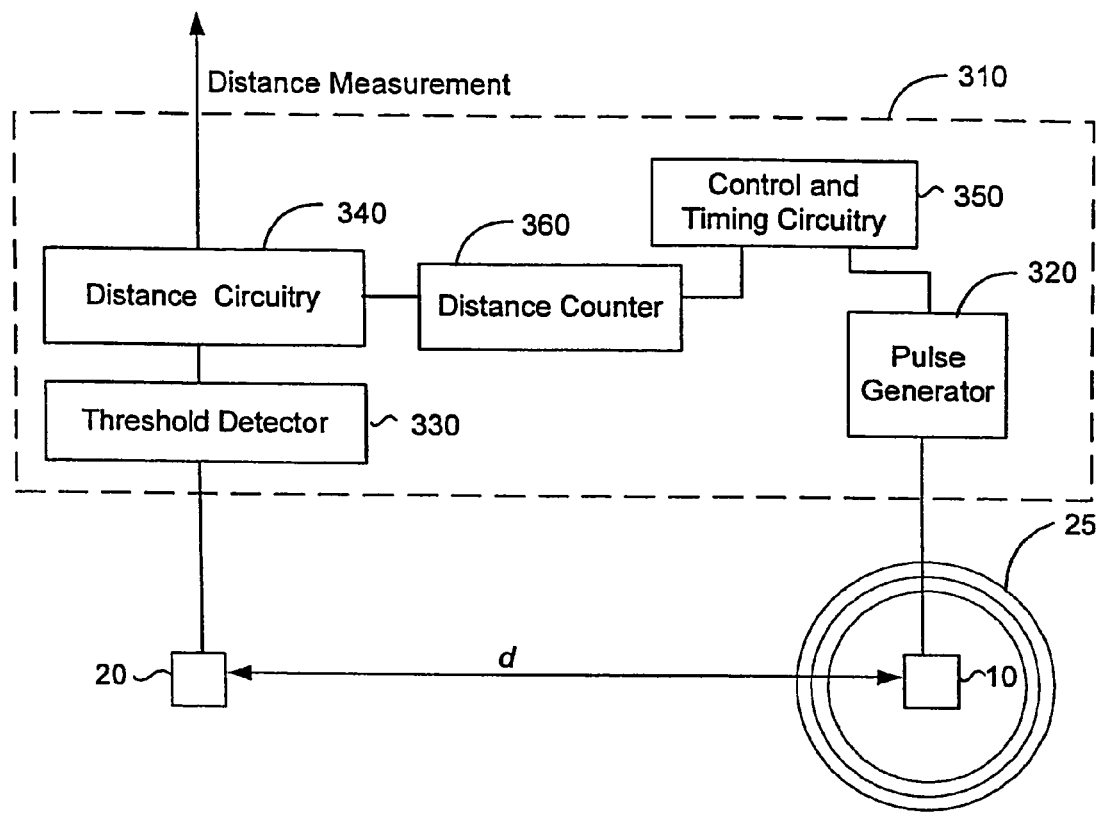
FIG. 3 is a functional diagram of an ultrasound ranging system.

FIG. 3 is a block diagram of an ultrasound ranging system 310 for measuring the distance between transducers 10,20. The ranging system 310 generally includes a pulse generator 320 coupled to the transmitting transducer 10, a threshold detector coupled 330 to the receiving transducer 20, and distance circuitry 340 coupled to the threshold detector 330. The pulse generator 320 may generate voltage pulses having a frequency of, e.g., 600 KHz. The threshold detector 330 detects signals from the receiving transducer 20 that are above a threshold level, e.g., a voltage level. The ranging system 310 further includes control and timing circuitry 350 coupled to the pulse generator 320, and a distance counter 360 coupled to the control and timing circuitry 350 and the distance circuitry 340. The distance counter 360 may be a digital counter driven by a clock. For ease of discussion, only one transmitting transducer 10 is shown. The more typical case of multiple transmitting transducers will be discussed later.

To measure the distance between the transducers 10,20, the control and timing circuitry 350 triggers the pulse generator 320 to generate and transmit a transmit pulse to the transmitting transducer 10. The transmitting transducer 10 converts the transmit pulse into an ultrasound pulse and transmits the ultrasound pulse 25. The control and timing circuitry 350 also triggers the distance counter 360 to begin counting from zero at the transmit time of the transmit pulse. The running count value of the distance counter 360 provides a measure of time from the transmission of the transmit pulse.

Figure 4:
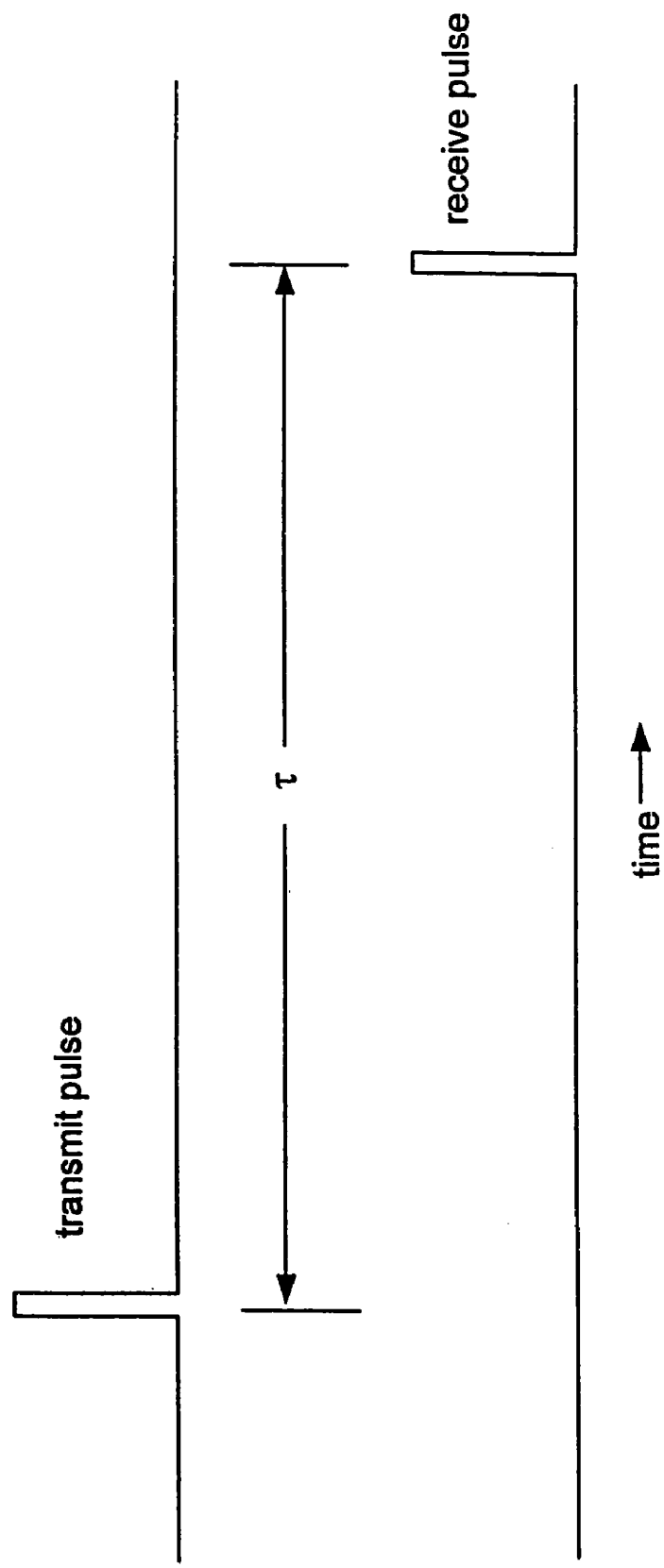
FIG. 4 is a timeline of a transmit pulse and a received pulse used to measure the time of flight of an ultrasound pulse.

After the ultrasound pulse 25 has been transmitted, the receiving transducer 20 receives the ultrasound pulse and converts the ultrasound pulse into a receive pulse, which is detected by the threshold detector 330. Upon detection of the receive pulse, the distance circuitry 340 reads the current count value from the distance counter 360. The read count value indicates the elapsed time between the transmission of the transmit pulse and the detection of the receive pulse, which corresponds to the time of flight, $\tau$, of the ultrasound pulse 25 between the transducers 10,20. This is illustrated in FIG. 4, which shows a timeline of the transmit pulse and the receive pulse. The read count value also provides a distance measurement between the transducers 10,20. This is because the distance, d, between the transducers 10,20 is proportional to the time of flight, $\tau$, of the ultrasound pulse 25, by $$d=v\tau$$

where v is the velocity of the ultrasound pulse 25. The distance circuitry 340 outputs the read count value as a distance measurement between the transducers 10,20.

In one embodiment, the distance circuitry 340 listens for the receive pulse within a time window, e.g., 100 μsec, after the transmit pulse has been transmitted. The time window may begin immediately or shortly after the transmit pulse has been transmitted. In determining the time of detection of the receive pulse, the distance circuitry 340 interprets the first signal that the threshold detector 330 detects within the time window as the receive pulse.

Figure 5:
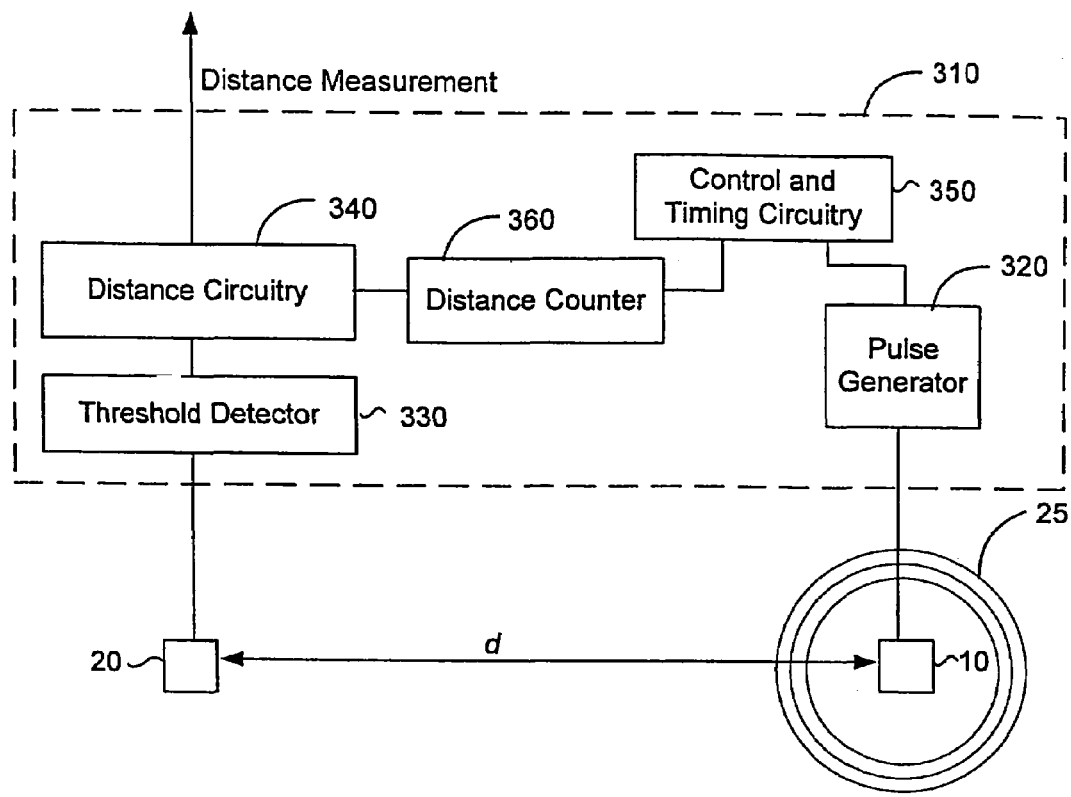
FIG. 5 is a diagram of the ultrasound ranging system of FIG. 3 in an environment containing a source of ultrasound interference.
Figure 5:
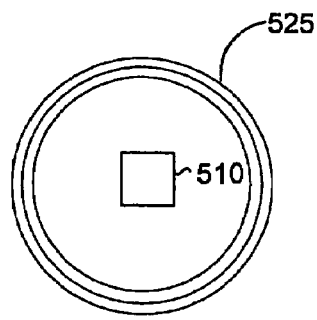

The operation of the ultrasound ranging system 310 in an environment containing ultrasound interference will now be described with reference to FIG. 5, in which a source 510 of ultrasound interference 525 is introduced. The source of ultrasound interference may be, e.g., an ultrasound imaging transducer. In the following discussion, it will be assumed that the ultrasound interference 525 is large enough in amplitude to be detected by the threshold detector 330.

When the ultrasound interference reaches the receiving transducer 20 before transmission of the transmit pulse, the distance circuitry 340 ignores the ultrasound interference. This is because the distance circuitry 340 does not listen for the receive pulse until after the transmit pulse has been transmitted.

Figure 6:
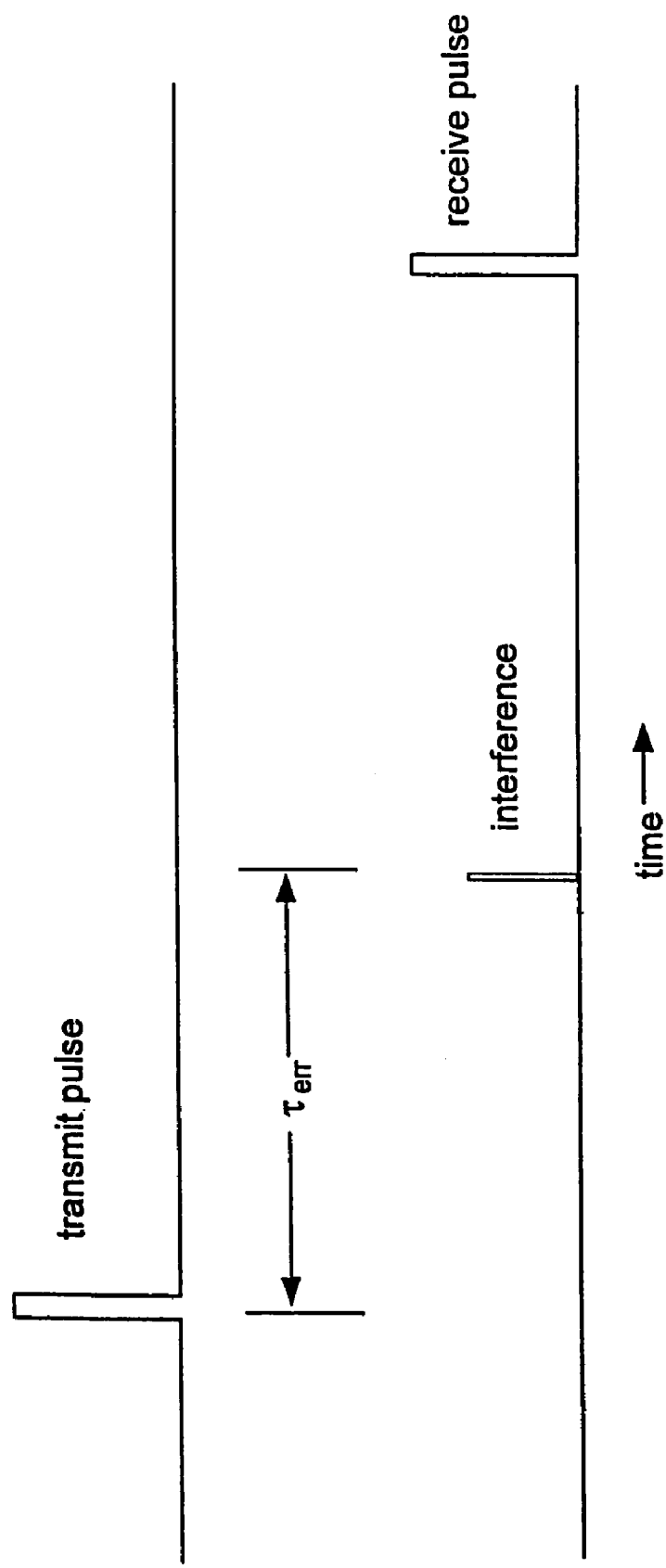
FIG. 6 is a timeline depicting the arrival of ultrasound interference between the transmit pulse and the receive pulse.

FIG. 6 is a timeline illustrating the case in which the ultrasound interference reaches the receiving transducer 20 between the transmit pulse and the receive pulse. When this occurs, the threshold detector 330 detects the ultrasound interference first. As a result, the distance circuitry 340 misinterprets the detected ultrasound interference as the receive pulse. This causes the distance measurement 350 unit to prematurely read the count value from the distance counter 360. In this case, the read count value indicates the time between the transmit pulse and the detection of the ultrasound interference. As a result, the read count value corresponds to an erroneous time of flight, $\tau_{err}$, that is shorter than the actually time of flight, $\tau$, of the ultrasound pulse, as illustrated in FIG. 6. This in turn causes the distance circuitry 340 to output a distance measurement that is shorter than the actual distance between the transducers 10,20.

When the ultrasound interference reaches the receiving transducer 20 after the receive pulse, the distance measurement circuitry 340 ignores the ultrasound interference. This is because the threshold detector 330 detects the receive pulse first. As a result, the distance circuitry 340 correctly reads the count value at the detection of the receive pulse.

Of the three cases discussed above, the only case in which the ranging system 310 is affected by the ultrasound interference is when the ultrasound interference reaches the receiving transducer 20 between the transmit pulse and the receive pulse. In this case, the distance circuitry 340 outputs a distance measurement that is shorter than the actual distance between the transducers 10,20. Thus, ultrasound interference causes the ranging system 310 to measure distances that are too short. The invention exploits this property to filter out erroneous distance measurements caused by ultrasound interference, as explained further below.

Figure 7:
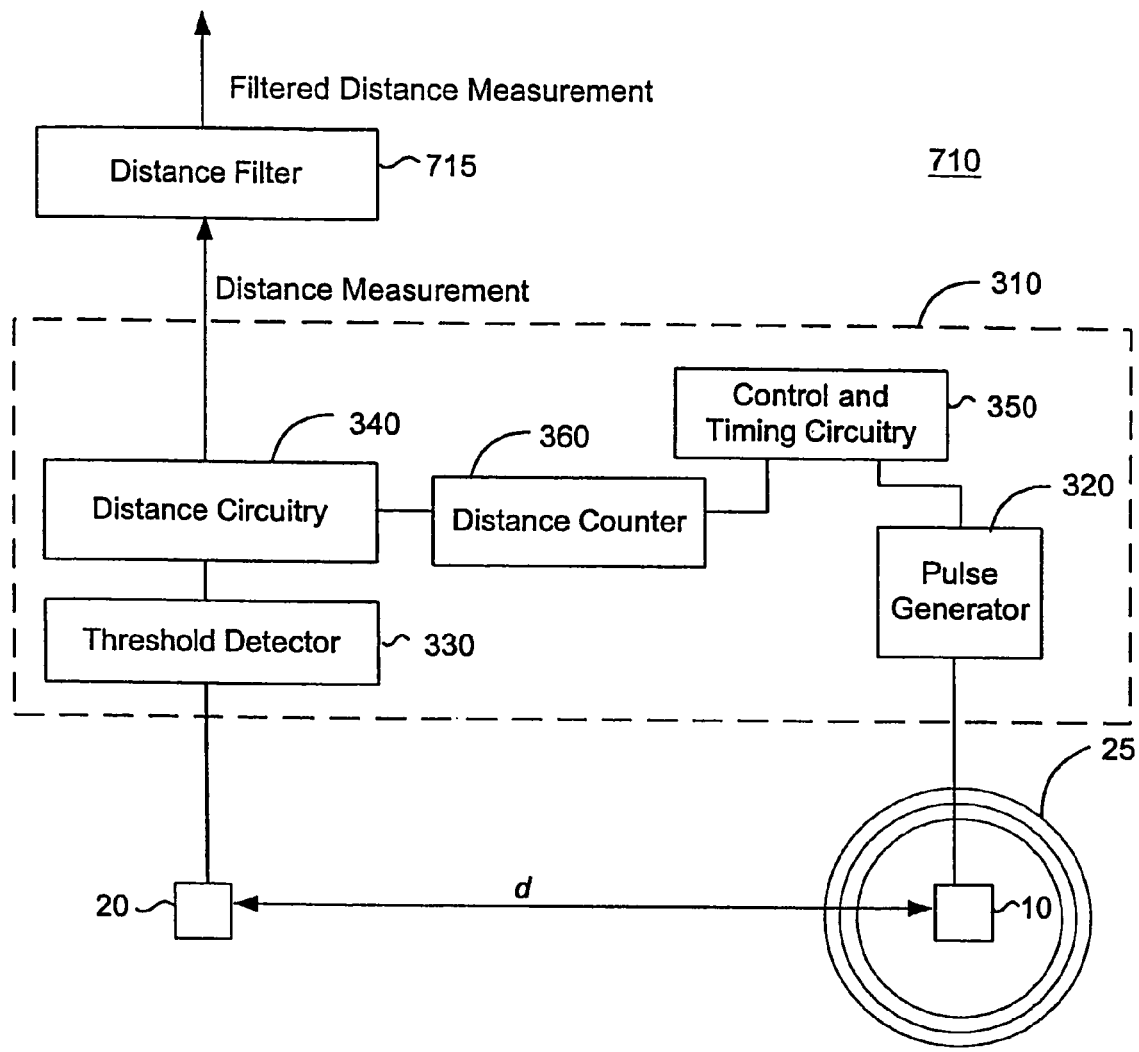
FIG. 7 is a functional diagram of the ultrasound ranging system further comprising a distance filter according to one embodiment of the invention.

FIG. 7 illustrates an embodiment of a system 710 for measuring the distance between transducers 10,20 further including a distance filter 715 coupled to the distance circuitry 340. In the preferred embodiment, the distance filter 715 is implemented in software, but can be implemented in firmware or hardware as well. In this embodiment, the control and timing circuitry 350 may continuously initiate distance measurements between the transducers 10,20 at regular intervals (e.g., once every 13 ms for a RPM system). Each time the control and timing circuitry 340 initiates a distance measurement, the distance circuitry 340 outputs a distance measurement to the distance filter 715. The filter 715 takes the last N distance measurements outputted by the distance circuitry 340, and outputs the maximum of the N distance measurements, where N is a positive integer (e.g., N=8).

The operation of the distance filter 715 can be represented as $$y(n)=\max[x(n), x(n-1), \ldots, x(n-N)]$$

where y(n) is the most recent output of the distance filter, x(n) is the most recent distance measurement from the distance circuitry 340, and max[ ] is a function that takes the maximum of the last N distance measurements from the distance circuitry 340 starting with the most recent distance measurement x(n).

The distance filter 715 filters out erroneous distance measurements caused by ultrasound interference. This is because ultrasound interference causes the distance circuitry 340 to output distance measurements that are shorter than the actual distance between the transducers 10,20. As a result, correct distance measurements outputted by the distance circuitry 340 will be larger than erroneous distance measurements caused by ultrasound interference. Therefore, when at least one of the last N distance measurements is correct, the maximum distance measurement outputted by the distance filter 715 will be one of the correct distance measurements. The distance filter 715 only outputs a distance error when every one of the last N distance measurements from the distance circuitry 340 is in error.

The distance filter 715 of the invention can significantly reduce distance errors due to ultrasound interference. This can be demonstrated by assuming that the probability of a distance error from the distance circuitry 340 due to ultrasound interference is P. In this case, the probability that every one of the last N distance measurements is in error is P to the Nth power. Since the distance filter 715 outputs a distance error only when every one of the last N distance measurements is in error, the probability of a distance error from the distance filter 715 is P to the Nth power, which can be significantly smaller than P. For example, if P equals 77% and N=8, the probability of a distance error from the distance circuitry 340 due to ultrasound interference is 77%, while the probability of a distance error from the distance filter due to ultrasound interference is 12.3%. Obviously increasing N can further reduce the probability of a distance error from the distance filter 715 due to ultrasound interference. However, increasing N may increase another type of distance error, as explained further below.

For the case in which the control and timing circuitry 350 initiates distance measurements at regular intervals (e.g., once every 13 milliseconds), the distance filter 715 outputs the maximum distance measurement over a finite measurement time window, M, of $$M = N\Delta t$$

where $\Delta t$ is the time between adjacent distance measurements and N is the number of distance measurements considered. For example, when $\Delta t$=13 ms and N=8, the measurement time window is 104 ms. In order for the distance filter 715 to provide a good approximation of the current distance between the transducers 10,20, the distance between the transducers 10,20 should remain relatively stable within the measurement window. This ensures that the maximum distance measurement within the measurement window provides a good approximation of the current distance between the transducers 10,20. When the distance between the transducers 10,20 varies within measurement window, the maximum distance may no longer closely approximate the current distance between the transducers 10,20. For example, when the distance between the transducers 10,20 decreases within the measurement window, the maximum distance will tend to be larger than the current distance between the transducers 10,20.

Therefore, there is tradeoff in increasing N. Increasing N decreases distance error due to ultrasound interference, but also increases distance error due to distance variation within the measurement window by increasing the size of the measurement window.

One way to reduce error caused by distance variation within the measurement window is to shorten the measurement window. This may be accomplished without decreasing N, e.g., by increasing the transmit rate of the system 710 in order to provide more distance measurements within a shorter period of time. This way, distance error due to distance variation can be reduced without increasing distance error due to ultrasound interference.

In another embodiment, the distance filter 715 computes a distance variation within the measurement window, and compares the computed distance variation to a threshold value. The distance filter 715 outputs the maximum distance measurement only when the distance variation within the measurement window exceeds the threshold value. Otherwise, the filter 715 outputs the most recent distance measurement from the distance circuitry 340.

The threshold value may be determined by the maximum that the distance between the transducers 10,20 can change within the measurement window due to movement between the transducers 10,20. For example, when the receiving transducer 20 is mounted on a catheter (not shown), the maximum change in distance may be determined by the maximum distance that a physician navigates the catheter within the measurement window. The threshold value may be represented as $$\text{threshold} = N\delta$$

where $\delta$ represents the maximum change in distance between adjacent distance measurements and N is the number of distance measurements considered.

Figure 8:
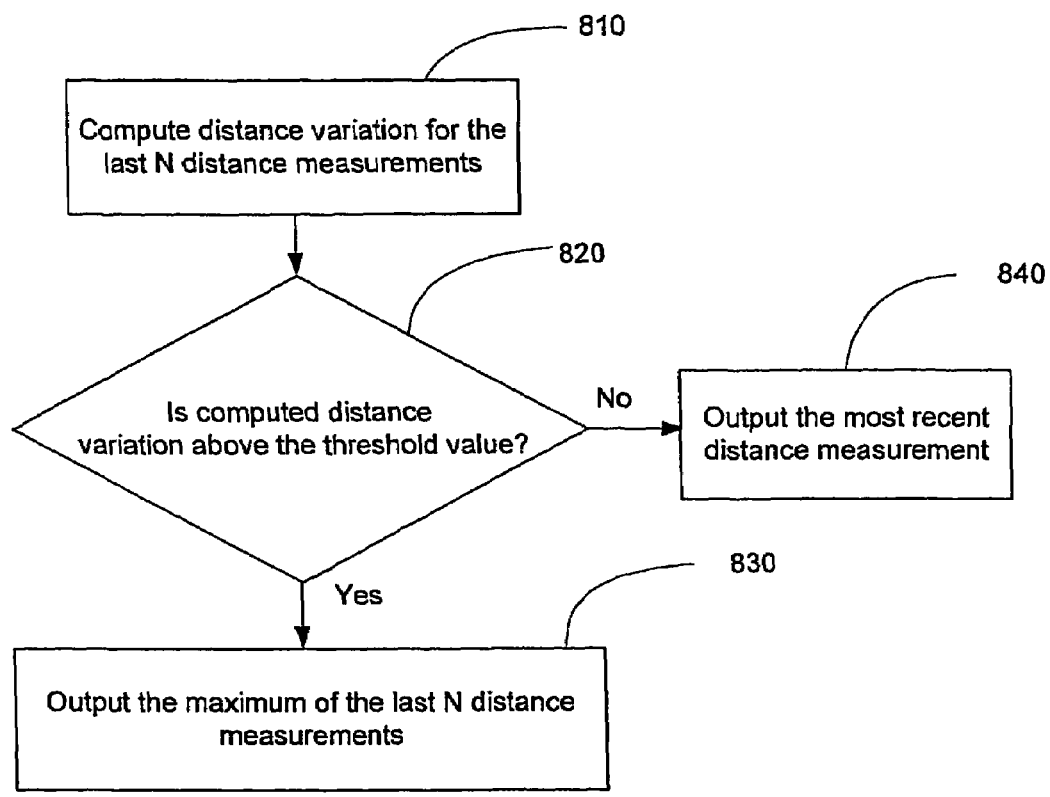
FIG. 8 is a flowchart illustrating the operation of a distance filter according to another embodiment of the invention.

The operation of the distance filter 715 according to this embodiment will now be described with reference to FIG. 8. In step 810, the distance filter 715 computes a distance variation for the last N distance measurements from the distance circuitry 340. The distance variation may be computed as the difference between the maximum and minimum of the last N distance measurements. This is represented as $$\text{range}(n) = \max[x(n), x(n-1), \ldots, x(n-N)] - \min[x(n), x(n-1), \ldots, x(n-N)]$$

where range(n) is the distance variation for the last N distance measurements, and x(n) is the most recent distance measurement from the distance circuitry 340. Other measures of distance variation may be used, such as computing the variance of the last N distance measurements. As another example, the second derivative of the last N distance measurements, which can be used to differentiate between rapid catheter movement and random interference can be taken. This is because rapid catheter movement, in the absence of interference, produces a distance measurement with a small second derivative, whereas random interference produces a distance measurement with a relatively large second derivative.

In step 820, the distance filter 715 compares the distance variation to the threshold value. If the distance variation is above the threshold value, the distance filter 715, at step 830, outputs the maximum of the last N distance measurements from the distance circuitry 340. Otherwise, at step 840, the distance filter 715 outputs the most recent distance measurement from the distance circuitry 340. The distance filter 715 repeats the steps in FIG. 8 for each subsequent distance measurement it receives from the distance circuitry 340.

Therefore, the distance filter 715 according to this embodiment reduces the unwanted side effects of increasing N by only outputting the maximum distance measurement when the computed distance variation exceeds the threshold value. In other words, the distance filter 715 only applies its maximum filtering function when the distance variation is most likely due to ultrasound interference, and not due to movement between the transducers 10,20.

Figure 9:
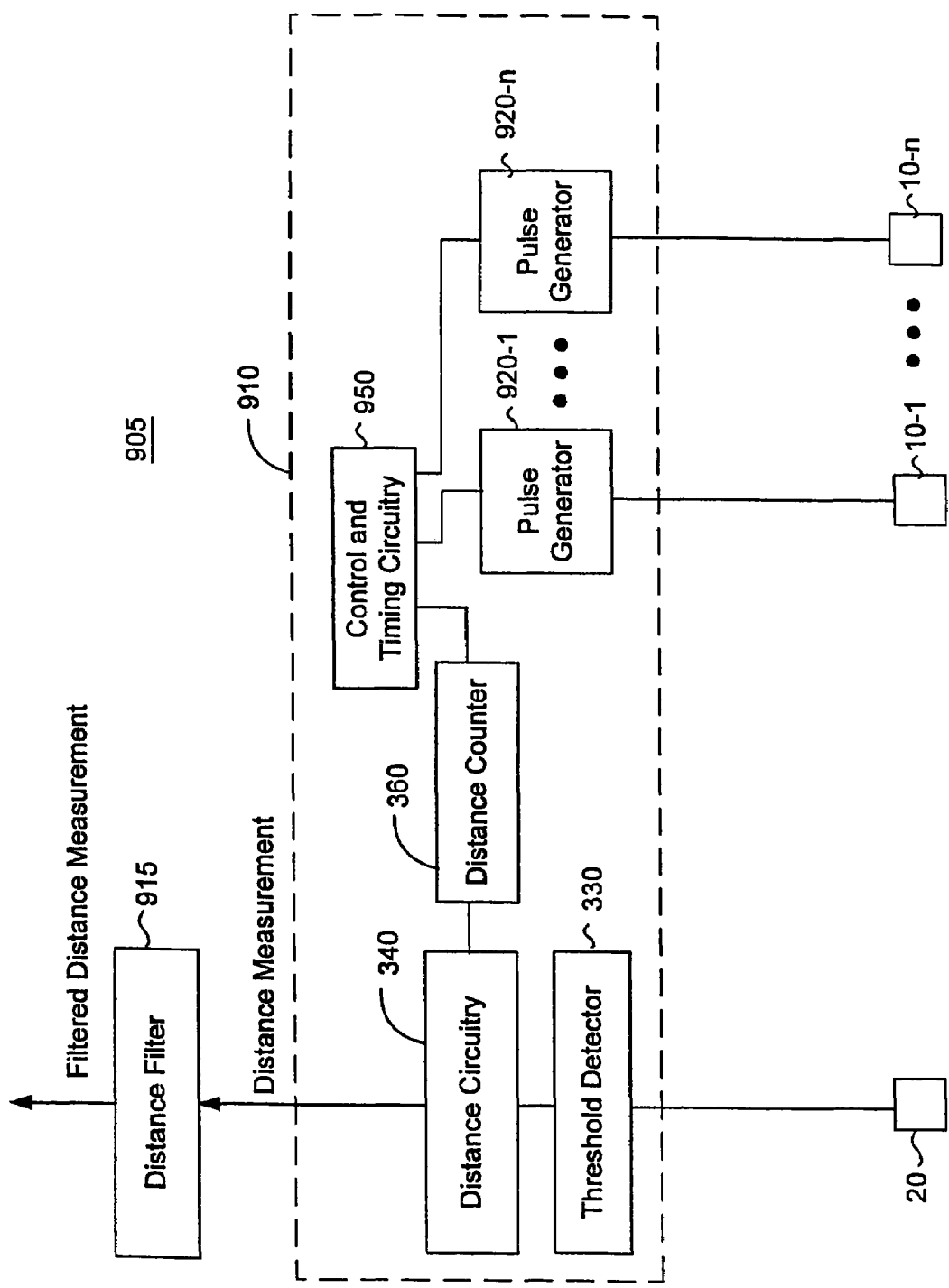
FIG. 9 is a functional block diagram of an ultrasound ranging system comprising multiple transmitting transducers according to another embodiment of the invention.

In the discussion above, the systems had one transmitting transducer. Many applications, such as ultrasound positional tracking, require multiple transmitting transducers. FIG. 9 illustrates an embodiment of the system 905, further including multiple transmitting transducers 10-1 to 10-n, where each of the transmitting transducers is coupled to a pulse generator 920-1 to 920-n. In this embodiment, the control and timing circuitry 950 sequentially initiates distance measurements between the receiving transducer 20 and each of the transmitting transducers 10-1 to 10-n.

In operation, the control and timing circuitry 950 sequentially triggers each one of the pulse generators 920-1 to 920-n to generate and transmit a transmit pulse to its respective transmitting transducer 10-1 to 10-n causing the transmitting transducer 10-1 to 10-n to transmit an ultrasound pulse (not shown). The transmit pulses may be spaced apart in time, e.g., 1 ms, so they do not interfere within one another.

For each transmit pulse, the control and timing circuitry 950 triggers the distance counter 360 to begin counting from zero at the transmit time of the transmit pulse. The control and timing circuitry 950 may also send data to the distance circuitry 340 identifying the corresponding transmitting transducer 10-1 to 10-n. After the transmit pulse has been transmitted, the distance circuitry 340 listens for a receive pulse within a time window, e.g., 100 µs. Upon detection of the receive pulse by the threshold detector 330, the distance circuitry 340 reads the current count value from the distance counter 360, which provides a distance measurement between the receiving transducer 20 and the corresponding transmitting transducer 10-1 to 10-n. The distance circuitry outputs the distance measurement to the distance filter 915. The distance circuitry 340 may also output data identifying the transmitting transducer 10-1 to 10-n corresponding to the distance measurement.

The distance filter 915 sequentially receives distance measurements corresponding to the distance between the ranging transducer 20 and each of the transmitting transducers 10-1 to 10-n from the distance circuitry 340. For each received distance measurement, the filter 915 identities the corresponding transmitting transducer 10-1 to 10-n. This may be accomplished several ways. For example, for each distance measurement, the control and timing circuitry 950 and/or the distance circuitry 340 may send data to the filter 915 identifying the corresponding transmitting transducer 10-1 to 10-n. Alternatively, the filter 915 may determine the identity of the corresponding transmitting transducer 10-1 to 10-2 according to the order in which it receives a sequence of distance measurements from the distance circuitry 340. For example, the filter 915 may assume that the first distance measurement in the sequence corresponds to transmitting transducer 10-1, the second distance measurement corresponds to transmitting transducer 10-2, and so forth.

In one embodiment, the distance filter 915 outputs a maximum distance for each of the transmitting transducers 10-1 to 10-n. In determining the maximum distance for each transmitting transducer 10-1 to 10-n, the filter 915 takes the maximum of the last N distance measurements for that particular transmitting transducer 10-1 to 10-n from the distance circuitry 340.

In another embodiment, the 915 filter also computes a distance variation for each transmitting transducer 10-1 to 10-n by computing a variation in the last N distance measurements for that particular transmitting transducer 10-1 to 10-n. The filter 915 may then compare the distance variation for each transmitting transducer 10-1 to 10-n to a threshold value. If the distance variation for a particular transmitting transducer 10-1 to 10-n is below the threshold value, then the filter 915 outputs the most recent distance measurement for that transmitting transducer 10-1 to 10-n. If the distance variation for a particular transmitting transducer 10-1 to 10-n is above the threshold value, then the filter 915 outputs the maximum of the last N distance measurements for that transmitting transducer 10-1 to 10-n.

Preferably, each time the filter 915 outputs a filtered distance measurement it includes data identifying the corresponding transmitting transducer 10-1 to 10-n. If implemented in software, the filter 915 is preferably embodied in several software modules—one for each transmitting transducer.

Figure 10:
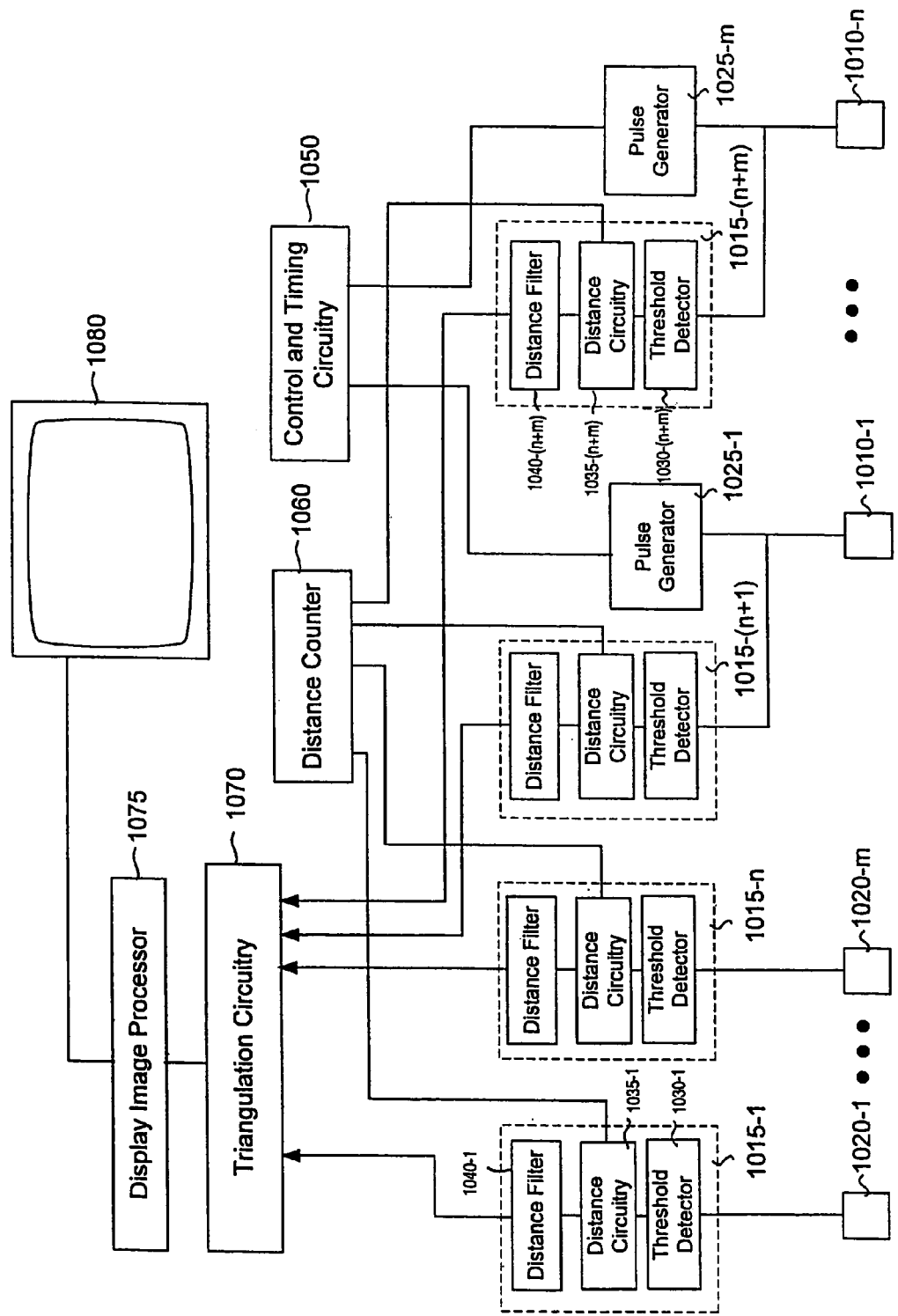
FIG. 10 is a functional block diagram of an ultrasound positional tracking system according to still another embodiment of the invention.

The invention is particularly well suited for use in ultrasound positional tracking systems to track the position of one or more devices (e.g., catheter). FIG. 10 illustrates an ultrasound positional tracking system 1005 according to an embodiment of the invention. The system 1005 includes two or more ranging transducers 1020-1 to 1020-m mounted on the medical device being tracked (not shown), and four or more reference transducers 1010-1 to 1010-n. Each of the ranging transducers 1020-1 to 1020-m acts as a receiving transducer and each of the reference transducers 1010-1 and 1010-n can act both as a receiving and transmitting transducer.

Figure 11:
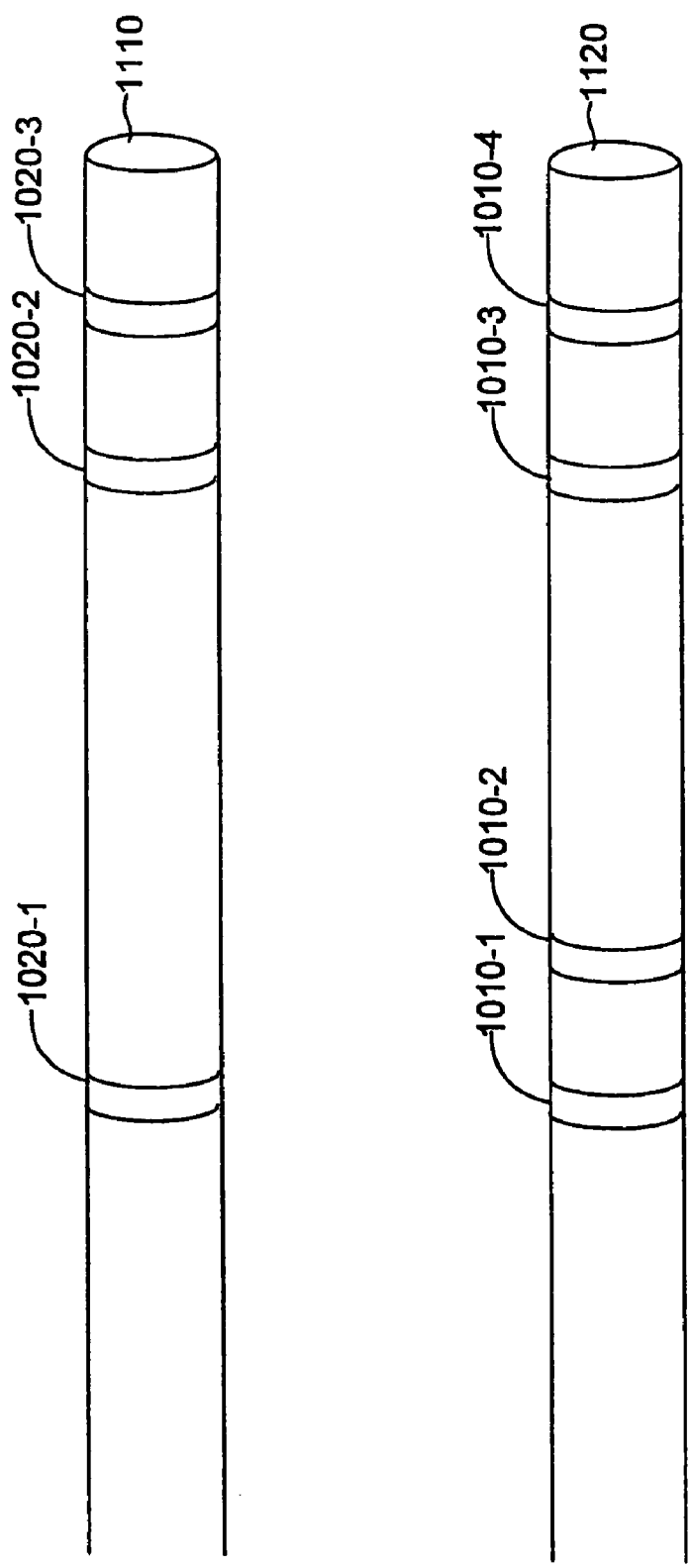
FIG. 11 illustrates examples of a medical catheter and a reference catheter that can be used with the system of FIG. 10.

FIG. 11 illustrates exemplary devices on which the ranging transducers 1020-1 to 1020-m and the reference transducers 1010-1 to 1010-n can be mounted. Three ranging transducers 1020-1 to 1020-3 are mounted on a distal portion of a catheter 1110 for performing medical and/or mapping procedures within the body. The catheter 1110 may be a mapping catheter, an ablation catheter, or the like. In this example, the ranging transducers 1020-1 to 1020-m take the form of annular ultrasound transducers. Also illustrated in FIG. 11 are four reference transducers 1010-1 to 1010-4 mounted on a distal portion of a reference catheter 1120.

Referring back to FIG. 10, the system 1005 also includes a distance measurement subsystem 1015-1 to 1015-(n+m) coupled to each of the ranging transducers 1020-1 to 1020-m and reference transducers 1010-1 to 1010-n, and a pulse generator 1025-1 to 1025-n coupled to each of the reference transducers 1010-1 to 1010-n. Each distance subsystem 1015-1 to 1015-(n+m) includes a threshold detector 1030-1 to 1030-(n+m), distance circuitry 1035-1 to 1035-(n+m) and a distance filter 1040-1 to 1040-(n+m) according to the invention for filtering out distance errors from the respective distance circuitry 1035-1 to 1035-(n+m). Notably, if implemented in software, the number of software modules for the distance filter 1040 will equal the product of the number of ranging transducers 1020 and the number of reference transducers 1010, i.e., m×n filter modules. The system 1005 further includes control and timing circuitry 1050 coupled to each of the pulse generators 1025-1 to 1025-n and a distance counter 1060 coupled to control and timing circuitry 1050 and each of the distance measurement subsystems 1015-1 to 1015-(n+m). The system 1005 also includes a triangulation circuitry 1070 for triangulating the positions of the ranging transducers 1020-1 to 1020-m and the reference transducers 1010-1 to 1010-n, a display image processor 1075 coupled to the triangulation circuitry, and a display 1080 coupled to the display image processor 1075. In the preferred embodiment, the triangulation circuitry 1070 is implemented in software, but can be implemented in firmware or hardware as well.

In operation, the control and timing circuitry 1050 sequentially triggers each one of the pulse generators 1025-1 to 1025-n to generate and transmit a transmit pulse to its respective reference transducer 1010-1 and 1010-n causing the reference transducer 1010-1 and 1010-n to transmit an ultrasound pulse. The transmit pulses may be spaced apart in time, e.g., 1 ms, so they do not interfere within one another.

For each transmit pulse, the control and timing circuitry 1050 triggers the distance counter 1060 to begin counting from zero at the transmit time of the transmit pulse. After the transmit pulse has been transmitted, each distance measurement subsystem 1015-1 to 1015-n listens for a receive pulse at its respective transducer 1020-1 to 1020-m and 1010-1 to 1010-n. Upon detection of a receive pulse by its respective threshold detector 1030-1 to 1030-(n+m), each distance circuitry 1035-1 to 1035-(n+m) reads the current count value from the distance counter, and outputs the read count value as a distance measurement to the respective distance filter 1040-1 to 1040-(n+m). Each distance filter 1040-1 to 1040-(n+m) filters out erroneous distance measurements from its respective distance circuitry 1035-1 to 1035-(n+m) due to ultrasound interference, and outputs the filtered distance measurements to the triangulation circuitry 1070. Each distance filter 1040-1 to 1040-(n+m), preferably, includes data identifying the corresponding receiving and transmitting transducer for each filtered distance measurement.

For each transmit pulse, the triangulation circuitry 1070 receives distance measurements between the reference transducer 1010-1 to 1010-n corresponding to the transmit pulse and each of the other reference transducers 1010-1 to 1010-n. The triangulation circuitry 1070 also receives distance measurements between the reference transducer 1010-1 to 1010-n corresponding to the transmit pulse and each of the ranging transducers 1020-1 to 1020-m.

The triangulation circuitry 1070 computes the relative positions between the reference transducers 1010-1 to 1010-n in 3-D space by triangulating the distance measurements between the references transducers 1010-1 to 1010-n. The triangulation circuitry 1070 then maps the relative positions between the reference transducers 1010-1 to 1010-n onto the 3-D coordinate system to provide a reference for tracking the positions of the ranging transducers 1020-1 to 1020-m in the 3-D coordinate system. The triangulation circuitry 1070 may employ any one of a number of mapping procedures as long as the mapping procedure preserves the relative positions between the reference transducers 1010-1 to 1010-n.

To track the positions of the ranging transducers 1020-1 to 1020-m within the 3-D coordinate system, the triangulation circuitry 1070 triangulates the relative positions of the ranging transducers 1020-1 to 1020-m to the reference transducers 1010-1 to 1010-n by triangulating the distance measurements between the ranging traducers 1020-1 to 1020-m and the reference traducers 1010-1 to 1010-n. The triangulation circuitry 1070 then determines the positions of the ranging transducers 1020-1 to 1020-m in the 3-D coordinate system based on the relative positions of the ranging transducers 1020-1 to 1020-m to the reference transducers 1010-1 to 1010-n and the known positions of reference transducers 1010-1 to 1010-n in the 3-D coordinate system.

Those skilled in the art will appreciate that the filters 1040-1 to 1040-(n+m) may be integrated in the triangulation circuitry 1070. This may be done, e.g., by modifying software in the triangulation circuitry 1070 to perform the filtering functions according to the invention. In this case, the distance measurements from each distance circuitry 1040-1 to 1040-(n+m) may be outputted directly to the triangulation circuitry 1070, which performs the filtering functions according to the invention before triangulating the positions of the transducers.

The triangulation circuitry 1070 outputs the positions of the ranging transducers 1020-1 to 1020-m and the reference transducers 1010-1 to 1010-n in the 3-D coordinate system to the display image processor 1075. The display image processor 1075 generates an image showing the position and orientation of the device being tracked in graphical form. The display image processor 1075 may do this by plotting the positions of the ranging transducers 1020-1 to 1020-m in the 3-D coordinate system and reconstructing a graphical representation of the device onto the plotted positions based on a pre-programmed graphical model of the device. The graphical model may include information on the relative positions of the ranging transducers on the device. The image may also show the position and orientation of the reference catheter 1120 (shown in FIG. 11) in graphical form. The display image processor 1075 may do this by plotting the positions of the reference transducers 1010-1 to 1010-n in the 3-D coordinate system and reconstructing a graphical representation of the reference catheter 1120 onto the plotted positions. The display image processor 1075 outputs the image to the display 1080, which displays the image to a physician.

Figure 12:
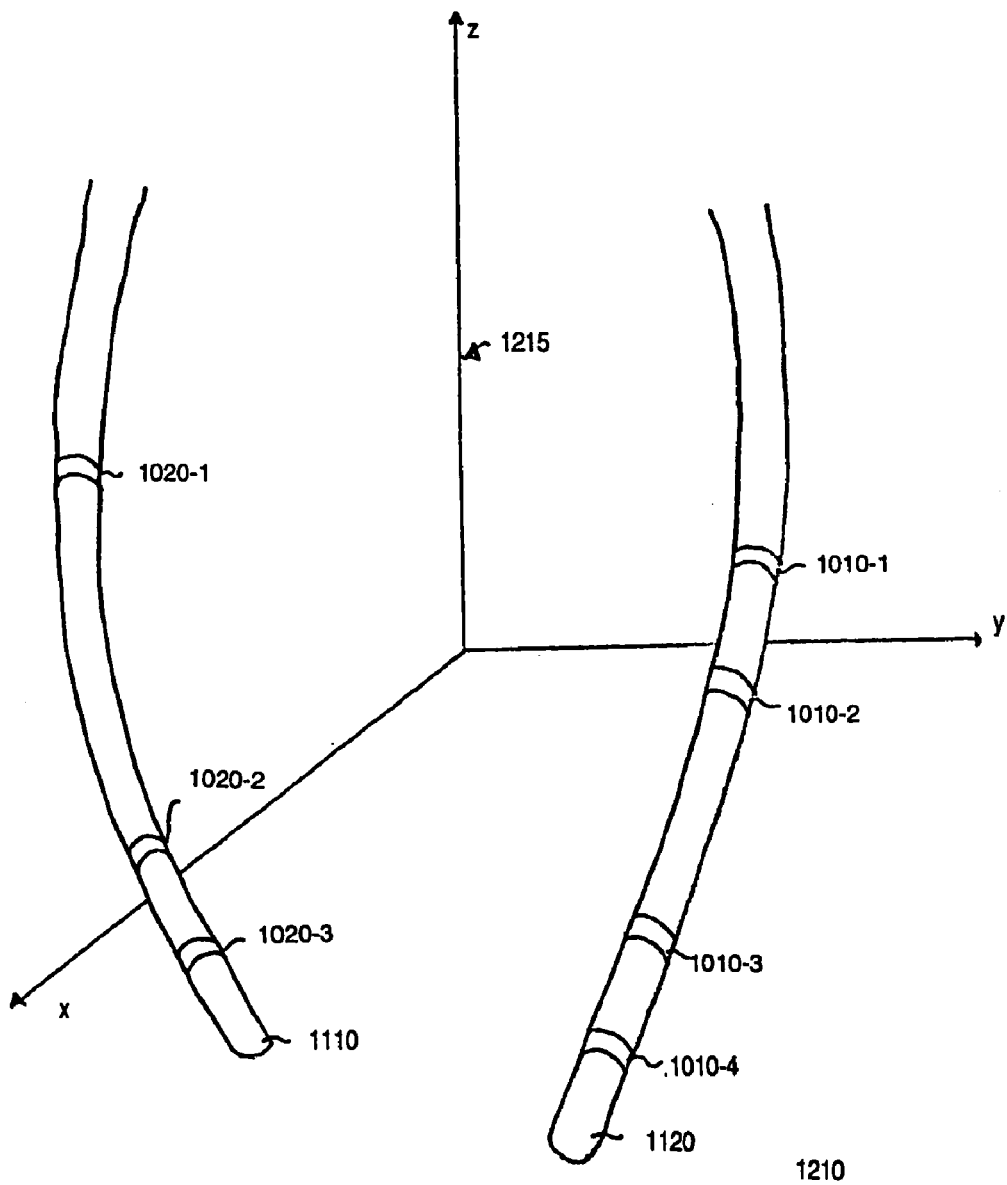
FIG. 12 illustrates an exemplary display image of the system of FIG. 10.

FIG. 12 shows an exemplary image 1210 in which the device being tracked is a medical catheter 1110 (shown in FIG. 11). The image 1210 includes graphical reconstructions of the medical catheter 1110 and the reference catheter 1120. The graphical reconstruction of the medical catheter 1110 is positioned and orientated in the image 1210 based on the tracked positions of the ranging transducers 1020-1 to 1020-3 in the 3-D coordinate system. Similarly, the graphical reconstruction of the reference catheter 1120 is positioned and orientated in the image 1210 based on the tracked positions of the reference transducers 1010-1 to 1010-4 in the 3-D coordinate system. The 3-D coordinate 1215 system may or may not be shown in the image 1210.

Even though one device was tracked in the above example, the ultrasound positional system 1005 may be used to track multiple devices equipped with ranging transducers. In addition, the display 1080 may display the position of anatomical landmarks in the 3-D coordinate system. This may be done, e.g., by positioning a mapping catheter equipped with ranging transducers at an anatomical landmark and recording the position of the anatomical landmark in the 3-D coordinate system based on the position of the mapping catheter. The position of the anatomical landmark in the. 3-D coordinate system may then be displayed and labeled on the display 1080. This enables a physician to more precisely guide devices within the body by referencing their tracked position on the display 1080 to the position of the anatomical landmark on the display 1080.

The display 1080 may also display a computer representation of body tissue in the 3-D coordinate system. This may be done, e.g., by moving a mapping catheter equipped with ranging transducers to different positions on the surface of the body tissue and recording these positions in the 3-D coordinate system. The image display processor 1075 may then reconstruct the computer representation of the body tissue in the 3-D coordinate system, e.g., by fitting an anatomical shell onto the recorded positions. The computer representation of the body tissue may then be displayed on the display 1080. This enables a physician to more precisely guide devices within the body by referencing their tracked position on the display 1080 to the computer representation of the body tissue on the display 1080. Additional details on this graphical reconstruction technique can be found in patent application Ser. No. 09/128,304 to Willis et al. entitled "A dynamically alterable three-dimensional graphical model of a body region", which is incorporated by reference.

An advantage of the ultrasound tracking system 1005 according to the invention is that the distance filters 1040-1 to 1040-(n+m) enable the tracking system 1005 to more reliably operate in an environment containing ultrasound interference. This is accomplished by filtering out distance errors due to ultrasound interference, thereby improving the accuracy of the distance measurements used to triangulate the positions of the ranging transducers 1020-1 to 1020-n and the reference transducers 1010-1 to 1010-n.

The invention is especially useful for using ultrasound tracking systems concurrently with ultrasound imaging. One advantage of using an ultrasound tracking system concurrently with ultrasound imaging is that it allows a physician to track the position of a device within a portion of the body while at the same time imaging the portion of the body using a ultrasound imager to provide additional information. Another advantage is that it allows the use of an ultrasound tracking system to track the position of a device having an ultrasound imager, e.g., an ultrasound imaging catheter.

The usefulness of the invention in using an ultrasound ranging system concurrently with ultrasound imaging will now be examined.

An ultrasound imager typically images the body by transmitting ultrasound pulses in the body and detecting the resulting echo pulses. The rate of transmission of the ultrasound pulses is constrained by two factors.

1. The distance that is to be imaged. This is because there must be enough time for the ultrasound energy to travel out to and back from the object being imaged.

2. Scattering interference. This is because the scattered energy from one ultrasound pulse must die out before the next ultrasound pulse can be transmitted.

The more rapidly the imaging transducer is pulsing, the higher the probability it will cause interference at an ultrasound tracking system. The probability of ultrasound interference occurring between two transducers of an ultrasound ranging system is $$P=(d/v)/T$$

where d is distance between the transducers, v is the velocity of ultrasound between the transducers, and T is the time between ultrasound pulses from the interfering ultrasound imager.

Figure 13:
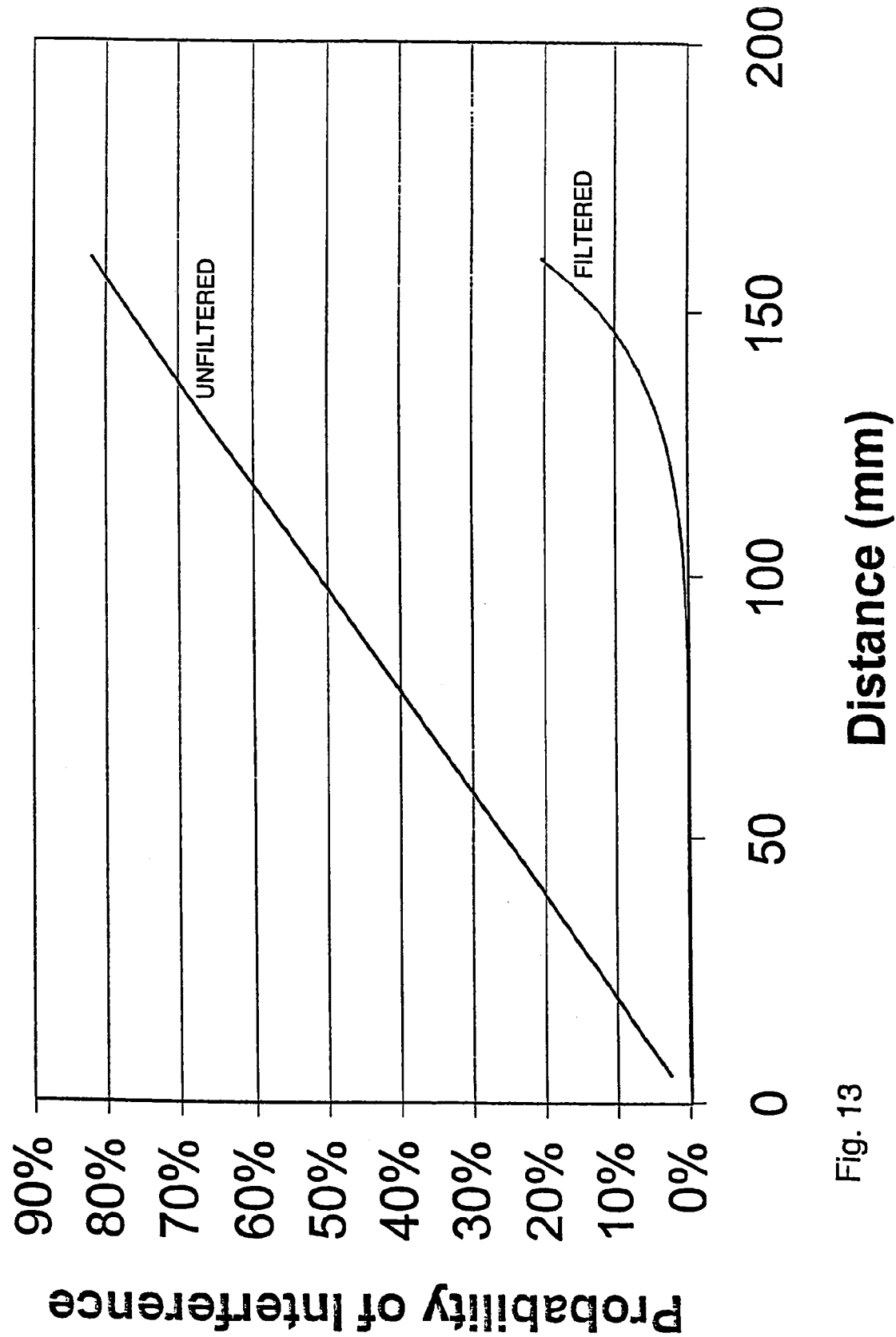
FIG. 13 is a graph illustrating the probability of a distance error with and without the filter of the invention as a function of distance between two transducers.

In one example, an Intracardiac Echocardiography ("ICE") catheter contains an ultrasound imager that transmits at a rate of 7680 Hz, which corresponds to a time, T, of 130 µ is between ultrasound pulses from the imager. FIG. 13 is a graph showing the probability of this particular ultrasound imager causing interference between two transducers of an ultrasound ranging system as a function of distance between the transducers. Without the distance filter of the invention, the probability of a distance measurement error is $P=(d/v)/T$, as given by the above equation. This is shown for $v=1.5$ mm/µsec and $T=130$ As by the curve labeled "unfiltered" in FIG. 13. The value $v=1.5$ mm/µsec is an approximation of the velocity of ultrasound in the body. With the distance filter of the invention, the probability of a distance measurement error is significantly reduced to P to the Nth power. This is shown for $N=8$ by the curve labeled "filtered" in FIG. 13.

Those skilled in the art will appreciate that various modifications may be made to the just described preferred embodiments without departing from the spirit and scope of the invention. For example, the distance filters of the invention are not limited for use with the particular ultrasound ranging systems described in the specification, and may be used with other ultrasound ranging systems susceptible to ultrasound interference. Therefore, the invention is not to be restricted or limited except in accordance with the following claims and their legal equivalents.

What is claimed is:

1. A distance measuring system, comprising:
   first and second transducers;
   an ultrasound ranging subsystem coupled to the first and second transducers for performing straight path distance measurements between the first and second transducers; and
   a filter coupled to the ultrasound ranging subsystem for receiving the distance measurements, comparing the distance measurements to each other, determining a relative ordering of the distance measurements based on the comparison, selecting one of the distance measurements based on the determined distance measurement ordering, and outputting the selected distance measurement as the distance between the first and second transducers.

2. The system of claim 1, wherein the distance measurement is only selected if it is greater than the minimum distance measurement.

3. The system of claim 1, wherein the distance measurement is only selected if it is the maximum distance measurement.

4. The system of claim 1, wherein the number of distance measurements compared is greater than 2.

5. The system of claim 1, wherein the ultrasound ranging subsystem further comprises:
   a pulse generator coupled to the first transducer for generating and transmitting transmit pulses to the first transducer;
   a threshold detector coupled to the second transducer for detecting receive pulses from the second detector; and
   measurement means coupled to the pulse generator and the threshold detector;
   wherein, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

6. The system of claim 5, wherein the measurement means comprises a digital counter for measuring the elapsed time.

7. The system of claim 1, further comprising a catheter on which at least one of the first and second transducers is mounted.

8. The system of claim 1, further comprising a processor coupled to the filter for determining the position of one of the first and second transducers in a three-dimensional coordinate system at least partially based on the outputted distance measurement.

9. A distance measuring system, comprising:
   first and second transducers;
   an ultrasound ranging subsystem coupled to the first and second transducers for performing straight path distance measurements between the first and second transducers; and
   a filter coupled to the ultrasound ranging subsystem for sequentially receiving the distance measurements, filtering ultrasound interference from the last N distance measurements, and outputting one of the N distance measurements as the distance between the first and second transducers based on the filtering of the distance measurements, wherein N is greater than 2.

10. The system of claim 9, wherein the ultrasound interference filtering comprises comparing the N distance measurements, and wherein the distance measurement is output based on the distance measurement comparison.

11. The system of claim 10, wherein the ultrasound interference filtering comprises determining a distance measurement that is greater than a minimum of the N distance measurements, and wherein the determined distance measurement is output as the distance between the first and second transducers.

12. The system of claim 9, wherein the ultrasound interference filtering comprises determining a maximum of the N distance measurements, and wherein the determined distance measurement is output as the distance between the first and second transducers.

13. The system of claim 9, wherein N is at least 8.

14. The system of claim 9, wherein the ultrasound ranging subsystem further comprises:
- a pulse generator coupled to the first transducer for generating and transmitting transmit pulses to the first transducer;
- a threshold detector coupled to the second transducer for detecting receive pulses from the second detector; and
- measurement means coupled to the pulse generator and the threshold detector;
- wherein, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

15. The system of claim 14, wherein the measurement means comprises a digital counter for measuring the elapsed time.

16. The system of claim 9, further comprising a catheter on which at least one of the first and second transducers is mounted.

17. The system of claim 9, further comprising a processor coupled to the filter for determining the position of one of the first and second transducers in a three-dimensional coordinate system at least partially based on the outputted distance measurement.

18. A distance measuring system, comprising:
- first and second transducers;
- an ultrasound ranging subsystem coupled to the first and second transducers for performing distance measurements between the first and second transducers; and
- a filter coupled to the ultrasound ranging subsystem for sequentially receiving the distance measurements, comparing the last N distance measurements to each other, determining a relative ordering of the last N distance measurements based on the comparison, detecting and comparing ultrasound interference against a threshold, selecting one of the last N distance measurements based on the determined distance measurement ordering if the detected ultrasound interference is above the threshold, selecting the Nth distance measurement if the detected ultrasound is below the threshold, and outputting the selected distance measurement as the distance between the first and second transducers.

19. The system of claim 18, wherein the selected one of the last N distance measurements must be greater than a minimum of the last N distance measurements.

20. The system of claim 18, wherein the selected one of the last N distance measurements must be the maximum of the last N distance measurements.

21. The system of claim 18, wherein N is greater than 2.

22. The system of claim 18, wherein N is at least 8.

23. The system of claim 18, wherein the ultrasound ranging subsystem further comprises:

- a pulse generator coupled to the first transducer for generating and transmitting transmit pulses to the first transducer;
- a threshold detector coupled to the second transducer for detecting receive pulses from the second detector; and
- measurement means coupled to the pulse generator and the threshold detector;
- wherein, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

24. The system of claim 23, wherein the measurement means comprises a digital counter for measuring the elapsed time.

25. The system of claim 18, further comprising a catheter on which at least one of the first and second transducers is mounted.

26. The system of claim 18, further comprising a processor coupled to the filter for determining the position of one of the first and second transducers in a three-dimensional coordinate system at least partially based on the outputted distance measurement.

27. The system of claim 18, wherein the ultrasound interference detection and comparison comprises computing a distance variation of the last N distance measurements and comparing the distance variation to a threshold value.

28. The system of claim 27, wherein the distance variation is the difference between the maximum and minimum of the last N distance measurements.

29. The system of claim 27, wherein the distance variation is the variance of the last N distance measurements.

30. The system of claim 27, wherein the distance variation is the second derivative of the last N distance measurements.

31. An ultrasound system, comprising:
- a first ultrasound-based subsystem for performing a distance measuring function; and
- a second ultrasound-based subsystem for generating ultrasound energy used to perform a function different from the distance measuring function;
- wherein the first ultrasound-based subsystem includes:
  - first and second transducers;
  - an ultrasound ranging subsystem coupled to the first and second transducers for performing distance measurements between the first and second transducers; and
  - a filter coupled to the ultrasound ranging subsystem for receiving the distance measurements, and filtering the ultrasound energy from the distance measuring function by comparing the distance measurements to each other, and selecting one of the distance measurements based on the comparison.

32. The system of claim 31, wherein the filter outputs the selected distance measurement as the distance between the first and second transducers.

33. The system of claim 32, wherein the distance measurement is only selected if it is greater than the minimum distance measurement.

34. The system of claim 32, wherein the distance measurement is only selected if it is the maximum distance measurement.

35. The system of claim 31, wherein the number of distance measurements is greater than 2.

36. The system of claim 35, wherein the measurement means comprises a digital counter for measuring the elapsed time.

37. The system of claim 31, wherein the ultrasound ranging subsystem further comprises:
a pulse generator coupled to the first transducer for generating and transmitting transmit pulses to the first transducer;
a threshold detector coupled to the second transducer for detecting receive pulses from the second detector; and
measurement means coupled to the pulse generator and the threshold detector;
wherein, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

38. The system of claim 31, further comprising a catheter on which at least one of the first and second transducers is mounted.

39. The system of claim 31, further comprising a processor coupled to the filter for determining the position of one of the first and second transducers in a three-dimensional coordinate system at least partially based on the outputted distance measurement.

40. The system of claim 31, wherein second ultrasound-based subsystem is an ultrasound imaging subsystem.

41. The system of claim 40, wherein the ultrasound energy filtering comprises comparing the N distance measurements to each other, and wherein the distance measurement is output based on the distance measurement comparison.

42. The system of claim 40, wherein N is at least 2.

43. The system of claim 42, wherein the measurement means comprises a digital counter for measuring the elapsed time.

44. The system of claim 40, further comprising a catheter on which at least one of the first and second transducers is mounted.

45. The system of claim 40, further comprising a processor coupled to the filter for determining the position of one of the first and second transducers in a three-dimensional coordinate system at least partially based on the outputted distance measurement.

46. The system of claim 40, wherein second ultrasound-based subsystem is an ultrasound imaging subsystem.

47. The system of claim 40, wherein the ultrasound ranging subsystem further comprises:
a pulse generator coupled to the first transducer for generating and transmitting transmit pulses to the first transducer;
a threshold detector coupled to the second transducer for detecting receive pulses from the second detector; and
measurement means coupled to the pulse generator and the threshold detector;
wherein, for each distance measurement, the measurement means triggers the pulse generator to generate and transmit a transmit pulse to the first transducer, measures the elapsed time between transmission of the transmit pulse and detection of a receive pulse by the threshold detector, and generates the distance measurement based on the measured elapsed time.

48. An ultrasound system, comprising:
a first ultrasound-based subsystem for performing a distance measuring function; and
a second ultrasound-based subsystem for generating ultrasound energy used to perform a function different from the distance measuring function;
wherein the first ultrasound-based subsystem includes:
first and second transducers;
an ultrasound ranging subsystem coupled to the first and second transducers for performing a plurality of distance measurements between the first and second transducers; and
a filter coupled to the ultrasound ranging subsystem for sequentially receiving the distance measurements, filtering the ultrasound energy from the last N distance measurements and outputting one of the N distance measurements as the distance between the first and second transducers based on the filtering of the distance measurements.

49. The system of claim 48, wherein the ultrasound energy filtering comprises determining a distance measurement that is greater than a minimum of the N distance measurements, and wherein the determined distance measurement is output as the distance between the first and second transducers.

50. The system of claim 48, wherein the ultrasound energy filtering comprises determining a maximum of the N distance measurements, and wherein the determined distance measurement is output as the distance between the first and second transducers.

* * * * *